United States Patent [19]

Panov et al.

[11] Patent Number: 5,756,861
[45] Date of Patent: May 26, 1998

[54] METHOD FOR PRODUCTION FOR PHENOL AND ITS DERIVATIVES

[75] Inventors: Gennady Ivanovich Panov; Alexandr Sergeevich Kharitonov; Galina Antolievan Sheveleva, all of Novosibirsk, Russian Federation

[73] Assignee: Monsanto Company, St. Louis, Mo.

[21] Appl. No.: 727,398

[22] PCT Filed: Apr. 12, 1995

[86] PCT No.: PCT/RU95/00066

§ 371 Date: Jan. 7, 1997

§ 102(e) Date: Jan. 7, 1997

[87] PCT Pub. No.: WO95/27691

PCT Pub. Date: Oct. 19, 1995

[30] Foreign Application Priority Data

Apr. 12, 1994 [RU] Russian Federation ............ 94013070

[51] Int. Cl.⁶ .................................................. C07C 37/00
[52] U.S. Cl. .................................................. 568/800
[58] Field of Search .......................... 568/800, 767, 568/771, 741

[56] References Cited

U.S. PATENT DOCUMENTS

| | | |
|---|---|---|
| 4,429,176 | 1/1984 | Chester et al. . |
| 4,559,314 | 12/1985 | Shihabi ............................ 502/71 |
| 4,982,013 | 1/1991 | Gubelmann et al. . |
| 5,001,280 | 3/1991 | Gubelmann et al. . |
| 5,055,623 | 10/1991 | Gubelmann et al. . |
| 5,077,026 | 12/1991 | Nair et al. ......................... 423/326 |
| 5,098,687 | 3/1992 | Skeels et al. ..................... 423/328 |
| 5,110,995 | 5/1992 | Kharitonov . |
| 5,367,099 | 11/1994 | Beck et al. ....................... 585/475 |
| 5,672,777 | 9/1997 | Kharitonov et al. . |

FOREIGN PATENT DOCUMENTS

| | | |
|---|---|---|
| 0 515 904 A1 | 5/1992 | European Pat. Off. . |
| 6-9464 | 1/1994 | Japan . |
| 2010790 | 4/1994 | Russian Federation . |
| 2116974 | 10/1983 | United Kingdom . |

OTHER PUBLICATIONS

Hafele et al., Catalysis on Solid Acids and Bases, DGMK-Tagungsbericht 9601, 1996.
Panov et al., Journal of Molecular Catalysis, 61 (1990) 85–97.
Iwamoto et al., Journal of Physical Chemistry, 87 (1983) 903–905.
Ono et al., Heterogeneous Catalysis and Fine Chemicals (1988) 75–82.
Suzuki et al., Chemistry Letters–Japan (1988) 953–956.
Burch et al., Applied Catalysis A: General 86 (1992) 139–146.
Burch et al., Applied Catalysis A: General 103 (1993) 135–162.
Burch et al., Applied Catalysis A: General 106 (1993) 167–183.
Panov et al., Applied Catalysis A: General 82 (1992) 31–36.
Panov et al., Applied Catalysis A: General 98 (1993) 1–20.
Kharitonov et al., Applied Catalysis A: General 98 (1993) 33–43.
Sobolev et al., Journal of Molecular Catalysis 84 (1993) 117–124.
Zholobenko et al., Mendeleev Commun (1993) 28–29.
Sobolev et al., Journal of Catalysis 139 (1993) 435–443.

*Primary Examiner*—Gary Geist
*Assistant Examiner*—Karl J. Pottlitz, Jr.
*Attorney, Agent, or Firm*—Howell & Haferkamp, L.C.

[57] ABSTRACT

A method for partial oxidation of aromatic compounds such as benzene, phenol, chlorobenzene, fluorobenzene, toluene, ethylbenzene and the like, with a molar deficiency of nitrous oxide over a catalyst such as a ZSM-5 or ZSM-11 zeolite. The method is advantageous for producing phenol from benzene at high production rates, high nitrous oxide conversion and high selectivity toward the production of phenol.

10 Claims, No Drawings

METHOD FOR PRODUCTION FOR PHENOL AND ITS DERIVATIVES

Disclosed herein is a method for the production of phenol and its derivatives by partial oxidation of benzene or a benzene derivative by nitrous oxide.

The production of phenol by partial oxidation of benzene using nitrous oxide over a variety of catalysts ranging from vanadium pentoxide on silica to zeolites, e.g. ZSM-5 and ZSM-11 zeolite catalysts, at elevated temperatures, e.g. 300° to 450° C., has been disclosed. In this reaction benzene is partially oxidized by an excess amount of nitrous oxide producing phenol and by-product nitrogen. See, for instance, Suzuki et al., 1988 Chemistry Letters of the Chemistry Society of Japan at pages 953–956. In U.S. Pat. No. 5,001, 280 Gubelmann et al. discloses the advantage of oxidizing benzene with nitrous oxide at 400° C. using a zeolite catalyst having a silica to alumina ratio greater than 90.

In U.S. Pat. No. 5,110,995 Kharitonov et al. disclose that changes in the molar ratio of benzene to nitrous oxide does not substantially affect the yields of phenol but declare a preference for a reaction mixture of stoichiometric composition. Although benzene derivatives can also be oxidized by nitrous oxide to provide the corresponding phenol derivative, phenol is the most important commodity chemical in the class with uses in the manufacture of phenolic resins and the synthesis of chemicals such as caprolactam and adipic acid.

The partial oxidation of benzene or a benzene derivative by nitrous oxide to phenol or a phenol derivative is highly exothermic. The liberation of significant quantities of heat, i.e. about 62 kilocalories per mole of phenol produced, leads to overheating of the catalyst resulting in lowering of reaction selectivity due to intensification of side reactions. Overheating can also diminish catalyst life.

Various approaches for avoiding overheating only make the process more complex. For instance, the reaction can be conducted in a tubular reactor with heat extracted by a circulating heat transfer fluid in an intertubular space. Alternatively, the reaction can be carried out in a fluid bed reactor equipped with internal heat exchangers. As the reaction becomes more exothermic, e.g. due to higher conversion, more complex equipment is required to remove the generated heat of reaction. For instance, in some cases the heat capacity of the reaction mixture is increased by introducing a high heat capacity component to reduce the level of adiabatic temperature increase.

Despite its simplicity, the use of high heat capacity components is rare because of requirements for such an additive component are very stringent. For example, in addition to having a high heat capacity, the component must also be inert under reaction conditions, must not poison the catalyst and must be easily separable from the reaction products. In the case of the oxidation of methanol to formaldehyde, Boreskov in Russian Pateny 804628 has suggested adding saturated hydrocarbons such as ethane and propane to the reaction mixture to absorb heat.

To avoid overheating in laboratory practice, the catalyst is usually placed in a tubular reactor of small diameter or diluted with quartz chips. The reaction is also often reported as being conducted using a small concentration of the starting materials. For instance, Burch et al. in Applied Catalysis A: General, 86 (1992)139–146, indicate that the optimal reaction mixture contains about 4 mole percent of benzene and a large excess of nitrous oxide. And, Gubelmann et al. discloses in U.S. Pat. No. 5,055,623 a reaction process using excess nitrous oxide where the reaction mixture has a molar ratio of nitrous oxide to benzene ranging from as 1 to 10. Among the drawbacks of these prior art reaction systems are overheating of the catalyst, low reactor capacity, low conversion of nitrous oxide and the generation of undesirable amounts of oxidized by-products such as hydroquinone resulting in a less than optimal selectivity towards the desired phenol product.

SUMMARY OF THE INVENTION

The present invention provides a simplified process for the catalytic partial oxidation of benzene or substituted benzene to the corresponding phenol with a multitude of advantages by employing a benzene and nitrous oxide feed stream that is rich in excess of the benzene reactant, i.e. has a molar deficiency of nitrous oxide. For instance, the process of this invention can allow for lower temperature rise of the reaction mixture due to adiabatic operation. The process of this invention can provide a higher selectivity in the desired oxidized product, e.g. phenol. The process of this invention can produce a reaction gas stream having a higher concentration of phenol. The process of this invention can provide a higher conversion of nitrous oxide. The process of this invention can provide for substantially higher catalyst production efficiency. And, the process of this invention can allow for operation using a non-explosive gas mixture.

DETAILED DESCRIPTION OF PREFERRED EMBODIMENTS

In the catalytic oxidation process of this invention, aromatic compounds, e.g. benzene or substituted benzene, is partially oxidized to the corresponding phenol or substituted phenol by reaction with nitrous oxide over a catalyst. The process can be conducted at elevated temperature, e.g. 250° to 500° C. or higher, e.g. up to at least 600° C. using a molar excess of the aromatic compound to be oxidized. For example, contrary to prior art practice, a reactant feed mixture according to this invention would have a molar deficiency of nitrous oxide, i.e. a molar ratio of nitrous oxide to aromatic compound less than 1, e.g. in the range of 0.95 to 0.01 or lower. In preferred aspects of this invention, the molar ratio of nitrous oxide to aromatic compound is less than 0.5. In the case of oxidation of benzene to phenol a preferred molar ratio of nitrous oxide to benzene is in the range of 0.9 to 0.01, often more preferably in the range of 0.1 to 0.01.

The prior art identifies a variety of catalysts that are useful in the partial oxidation of benzene, e.g. vanadium pentoxide on silica and acidified zeolites. For many applications, ZSM-5 and ZSM-11 zeolite catalysts containing a catalytically effective amount of iron have significant advantages over other catalysts. Preferred catalysts are acidified ZSM-5 and ZSM-11 zeolite containing iron. The productivity of the process can be enhanced by using a zeolite that has been hydrothermally treated, e.g. exposed to up to 100% water vapor in air at about 500° to 900° C. for about 2 hours.

A major distinction of the process of this invention is that the reaction is carried out with a molar deficiency of the nitrous oxide. In addition to vaporized aromatic compound and nitrous oxide the reactant gas feed to the catalyst can contain a variety of other gases as diluents or contaminants. Diluents typically will not adversely effect the desired reaction to produce the oxidized aromatic product, e.g. phenol, and typically comprise helium, argon, nitrogen, carbon dioxide or other such gases or mixtures thereof. Contaminants are characterized as species that adversely effect the desired reaction to produce the oxidized aromatic product whether by participating in a competing reaction or poisoning of the catalyst. The amount of contaminants is preferably very low, but in view of the practical difficulty of providing pure gases in industrial applications, certain low levels of contaminants can be tolerated. Contaminant typically found in industrial gas streams that can be tolerated at low levels include water vapor, oxygen, carbon monoxide, nitric oxide, nitrogen dioxide and other organic species.

In addition to benzene the aromatic compound can be any of a variety of substituted benzenes such as phenol, fluorobenzene, chlorobenzene, toluene, ethylbenzene and similar compounds having an aromatic ring with a substitutable hydrogen atom on the ring. The process can be used to produce polyols, e.g. hydroquinone, resorcinol and catechol, by oxidation of phenol. Thus, when phenol is produced from oxidation of benzene, the phenol product can be further oxidized by contact with the catalyst. Undesirable production of polyols can be avoided by employing a low ratio of nitrous oxide to aromatic compound, e.g. about 0.5 or lower, and by minimizing catalyst residence time. Similarly a mixture of polyols can be prepared by extending catalyst residence time. Generally, it is preferred to keep catalyst contact time at a low level to preclude production of unwanted polyols. Such residence time can readily be determined by a person skilled in the art by routine experimentation in view of reaction conditions, catalyst activity, feed compositions, catalyst bed size and the like.

The benefits and advantages of the process of this invention are illustrated by reference to the following examples of various conditions in which benzene is oxidized to phenol in a flow reactor having an iron-containing ZSM-5 zeolite catalyst. The catalyst characterized by the silica to alumina ratio ($SiO_2/Al_2O_3$) of 100 and containing 0.45 weight percent (wt %) $Fe_2O_3$ was synthesized using the procedures disclosed by Ione et al. in *Usp. Khimii* (Russian Chemical Review), 1987, Vol. 56, No. 3, p. 393; the catalyst was segregated to provide a 0.5–1.0 mm fraction. A flow reactor was prepared by loading 10 cc of the zeolite catalyst into a quartz reactor tube having a 1.2 cm inside diameter. Gas phase temperature determined from a thermocouple in a thermowell located in the catalyst bed was used to determine overheating "$\Delta T$" of the catalyst due to heat generated in the exothermal reaction. Gas chromatography was used to determine the composition of feed and reaction products. The results of feed and product gas analysis were averaged and used to calculate reaction parameters: the selectivity of the reaction for producing phenol "S", the concentration of phenol at the exit from the reactor "C", the conversion of nitrous oxide "X" and the catalyst productivity "P". The reaction conditions and calculated reaction parameters are reported in the following table.

COMPARATIVE EXAMPLES 1–3

A gas mixture containing 4.1 mole percent (mol %) benzene, 20.5 mol % nitrous oxide and 75.4 mol % nitrogen and having a heat capacity of 7.9 calories per mole per degree Celsius (cal/mol deg) was passed through the flow reactor to the catalyst at 12 liters per hour (l/hr) for two hours. Oxidation products in the product gas at the exit of the reactor were determined to comprise phenol, carbon dioxide, carbon monoxide, water and trace amounts of dihydroxybenzenes. The trace amounts of the dihydroxybenzenes were not accounted for in the calculation of reaction selectivity.

EXAMPLES 4–6

Essentially following the procedures of Examples 1–3 the oxidation of benzene was repeated except that a portion of the nitrogen was replaced with ethane to provide a reaction mixture containing 55 mol % ethane as a feed component to increase heat capacity of the reaction mixture to 11.0 cal/mol deg. Reference to the reaction parameters reported in the table shows that the use of ethane as a diluent provides a slight advantage in selectivity for phenol at higher temperatures as compared to the use of nitrogen as a diluent.

EXAMPLES 7–9

Essentially following the procedures of Examples 4–6 the oxidation of benzene was repeated except that the ethane was replaced with excess benzene. Reference to the reaction parameters reported in the table shows that the use of excess benzene (that is, a molar deficiency of nitrous oxide) provides a surprising advantage with unexpectedly higher selectivity for phenol, at higher concentration in the product gas, at higher conversion of nitrous oxide and higher catalyst productivity.

EXAMPLES 10–12

Essentially following the procedures of Examples 1–3, the oxidation of benzene was repeated except that all of the diluent nitrogen was replaced with excess benzene and the amount of nitrous oxide reduced to provide a reaction mixture with a molar ratio of benzene to nitrous oxide of 9:1 and a heat capacity of 18.9 cal/mol deg. Reference to the reaction parameters reported in the table shows that higher levels of excess benzene provide surprisingly greater advantage, including conditions allowing 100% selectivity of phenol and 100% conversion of nitrous oxide which eliminates any need for nitrous oxide removal/recycle from the product gas.

EXAMPLES 13–15

Essentially following the procedures of Examples 10–12, the oxidation was repeated at a lower reaction mixture flow of 6 l/hr. Reference to the reaction parameters reported in the table shows that adjusting reaction mixture flow rate with excess benzene can advantageously effect reaction. performance.

| Ex. | Composition of the reaction mixture | | | Cp | Gas Flow | Temperature (c) | | S | C | X | P |
|---|---|---|---|---|---|---|---|---|---|---|---|
| | $C_6H_5$ | $N_2O$ | $N_2$ | (a) | (b) | T | $\Delta T$ | % | % | % | |
| 1 | 4.1 | 20.5 | 75 | 7.9 | 12.0 | 300 | 8 | 95 | 0.6 | 7 | 0.05 |
| 2 | 4.1 | 20.5 | 75 | 7.9 | 12.0 | 350 | 30 | 89 | 1.0 | 19 | 0.08 |
| 3 | 4.1 | 20.5 | 75 | 7.9 | 12.0 | 400 | 50 | 81 | 1.05 | 31 | 0.09 |
| 4 | 4.0 | 21 | 20* | 11.0 | 12.0 | 300 | 5 | 95 | 0.6 | 7 | 0.05 |

-continued

| | Composition of the reaction mixture | | | Cp | Gas Flow | Temperature (c) | | S | C | X | |
|---|---|---|---|---|---|---|---|---|---|---|---|
| Ex. | $C_6H_5$ | $N_2O$ | $N_2$ | (a) | (b) | T | ΔT | % | % | % | P |
| 5 | 4.0 | 21 | 20$^e$ | 11.0 | 12.0 | 350 | 21 | 92 | 0.95 | 14 | 0.08 |
| 6 | 4.0 | 21 | 20$^e$ | 11.0 | 12.0 | 400 | 28 | 85 | 1.05 | 25 | 0.09 |
| 7 | 61 | 20 | 19 | 15.2 | 12.0 | 300 | 5 | 100 | 1.8 | 11 | 0.15 |
| 8 | 61 | 20 | 19 | 15.2 | 12.0 | 350 | 27 | 97 | 4.1 | 37 | 0.35 |
| 9 | 61 | 20 | 19 | 15.2 | 12.0 | 400 | 35 | 95 | 5.5 | 60 | 0.46 |
| 10 | 90 | 10 | 0 | 18.9 | 9.0 | 350 | 18 | 100 | 4.5 | 58 | 0.28 |
| 11 | 90 | 10 | 0 | 18.9 | 9.0 | 400 | 23 | 98 | 5.3 | 93 | 0.33 |
| 12 | 90 | 10 | 0 | 18.9 | 9.0 | 430 | 27 | 97 | 5.4 | 100 | 0.39 |
| 13 | 90 | 10 | 0 | 18.9 | 6.0 | 350 | 12 | 100 | 5.0 | 70 | 0.21 |
| 14 | 90 | 10 | 0 | 18.9 | 6.0 | 400 | 15 | 98 | 5.4 | 96 | 0.22 |
| 15 | 90 | 10 | 0 | 18.9 | 6.0 | 430 | 16 | 98 | 5.5 | 100 | 0.23 | a: heat capacity (cal/mol deg)
b: gas flow rate (liters/hour)
c: temperature (°C.)
d: productivity (g phenol per g catalyst per hour)
e: diluent gases: 20% nitrogen and 55% of ethane While specific embodiments have been described herein, it should be apparent to those skilled in the art that various modifications thereof can be made without departing from the true spirit and scope of the invention. Accordingly, it is intended that the following claims cover all such modifications within the full inventive concept.

What is claimed is:

1. A method for oxidizing an aromatic compound using nitrous oxide, comprising contacting a solid catalyst with a gaseous mixture of the aromatic compound and nitrous oxide, wherein the nitrous oxide is present in a molar deficiency.

2. A method according to claim 1 wherein the molar ratio of nitrous oxide to aromatic compound is in the range of 0.9 to 0.01.

3. A method according to claim 1 wherein said aromatic compound is benzene or substituted benzene.

4. A method according to claim 1 wherein said catalyst is a zeolite.

5. A method according to claim 4 wherein said catalyst is a ZSM-5 or ZSM-11 zeolite catalyst.

6. A method according to claim 5 wherein said aromatic compound is benzene.

7. A method according to claim 6 wherein the molar ratio of nitrous oxide to benzene is in the range of 0.1 to 0.01.

8. A method according to claim 7 wherein the gaseous mixture contacts said catalyst at a temperature in the range of 250° to 600° C.

9. A method according to claim 8 wherein said gaseous mixture comprises benzene, nitrous oxide and one or more gases selected from the group consisting of helium, nitrogen, nitric oxide, nitrogen dioxide, carbon dioxide and argon.

10. A method according to claim 9 wherein said catalyst is an acidified ZSM-5 or ZSM-11 zeolite containing iron.

* * * * *

UNITED STATES PATENT AND TRADEMARK OFFICE
CERTIFICATE OF CORRECTION

PATENT NO. : 5,756,861
DATED : May 26, 1998
INVENTOR(S) : Panov et al.

It is certified that error appears in the above-identified patent and that said Letters Patent is hereby corrected as shown below:

Title page, and column 1, line 1; The title should read "METHOD FOR PRODUCTION OF PHENOL AND ITS DERIVATIVES", rather than "METHOD FOR PRODUCTION FOR PHENOL AND ITS DERIVATIVES".

In the column headings of the table at the bottom of column 4 and again at the top of column 5, the term "$C_6H_5$" should be replaced by --- $C_6H_6$ ---.

Signed and Sealed this

First Day of September, 1998

*Attest:*

BRUCE LEHMAN

*Attesting Officer*     *Commissioner of Patents and Trademarks*